United States Patent [19]

Hubele

[11] 4,000,303
[45] Dec. 28, 1976

[54] IMIDAZOLIDINE-2,4-DIONE DERIVATIVES AND THEIR USE AS PESTICIDES

[75] Inventor: Adolf Hubele, Magden, Switzerland

[73] Assignee: Ciba-Geigy Corporation, Ardsley, N.Y.

[22] Filed: Mar. 15, 1976

[21] Appl. No.: 666,731

Related U.S. Application Data

[62] Division of Ser. No. 500,983, Aug. 27, 1974, Pat. No. 3,960,883.

[30] Foreign Application Priority Data

Sept. 3, 1976  Switzerland .................. 12605/76
Mar. 14, 1976  Switzerland .................. 3567/76

[52] U.S. Cl. .................................. 424/273
[51] Int. Cl.² ................................ A01N 9/22
[58] Field of Search ....................... 424/273

[56] References Cited

UNITED STATES PATENTS 3,178,447   4/1965   Kohn .................. 260/309.5

Primary Examiner—Ethel G. Love
Attorney, Agent, or Firm—Frederick H. Rabin

[57] ABSTRACT

Imidazolidine-2,4-dione derivatives of formula I

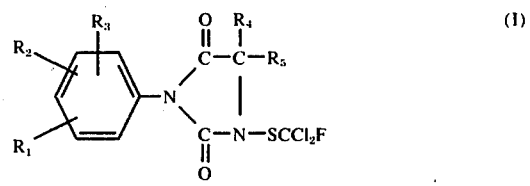

wherein $R_1$ and $R_2$ each independently represent hydrogen, halogen, $C_1$-$C_3$-alkyl, nitro, $C_1$-$C_3$-haloalkyl or $C_1$-$C_3$-alkoxy, $R_3$ represents hydrogen, halogen or methyl, and $R_4$ and $R_5$ each independently represent hydrogen or $C_1$-$C_3$-alkyl, whereby if one of the symbols $R_1$, $R_2$ or $R_3$ is hydrogen the two others cannot simultaneously be halogen atoms in the meta-position with respect to the amino group which are useful as pesticides.

11 Claims, No Drawings

4,000,303

IMIDAZOLIDINE-2,4-DIONE DERIVATIVES AND THEIR USE AS PESTICIDES

This is a division of application Ser. No. 500,983 filed on Aug. 27, 1974, now U.S. Pat. No. 3,960,883.

The present invention relates to imidazolidine-2,4-dione derivatives, to processes for the preparation thereof as well as to agents and processes for the control of pests.

The new imidazolidine-2,4-dione derivatives correspond to formula I

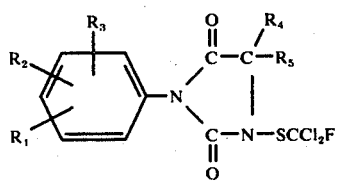

wherein
$R_1$ and $R_2$ each independently represent hydrogen, halogen, $C_1$-$C_3$-haloalkyl or $C_1$-$C_3$-alkoxy,
$R_3$ represents hydrogen, halogen or methyl, and
$R_4$ and $R_5$ each independently represent hydrogen or $C_1$-$C_3$-alkyl, whereby if one of the symbols $R_1$, $R_2$ or $R_3$ is hydrogen the two others cannot simultaneously be halogen atoms in the meta-position with respect to the amino group.

Alkyl and alkoxy radicals $R_1$ and $R_2$ and alkyl radicals $R_4$ and $R_5$ can be straight-chain or branched-chain, i.e. they can be methyl, ethyl, n-propyl or iso-propyl and methoxy, ethoxy, n-propoxy or iso-propoxy. By halogen is meant fluorine, chlorine, bromine and iodine. Haloalkyl groups such as $R_1$ and $R_2$ consist of an alkyl group, such a methyl, ethyl, n-propyl or iso-propyl, substituted by 1 to 3 halogen atoms (i.e. fluorine, chlorine, bromine or iodine), e.g. trifluoromethyl.

A particularly interesting group of compounds of formula I are those wherein $R_4$ and $R_5$ represent hydrogen. Compounds especially preferred are those of formula I wherein $R_1$ and $R_2$ each independently represent hydrogen, chlorine, methyl or trifluoromethyl, $R_3$ represents hydrogen, chlorine or methyl, with the proviso that of the substituents $R_1$, $R_2$ and $R_3$ two cannot simultaneously be halogen atoms in the meta-position with respect to the amino group if the third substituent is hydrogen.

The compounds of formula I can be prepared according to the invention by a process in which a. a compound of formula II

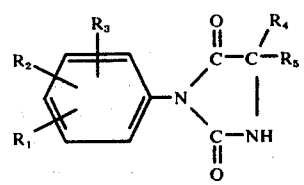

is reacted in the presence of an acid-binding agent with a compound of formula III

ClSCCl$_2$F      (III), or b. a compound of formula IV

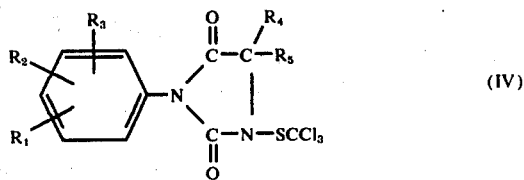

is reacted with anhydrous hydrofluoric acid, in order to exchange in the trichloromethylthio side chain a chlorine atom for a fluorine atom. In formulae II, III and IV, the symbols $R_1$, $R_2$, $R_3$, $R_4$ and $R_5$ have the meanings given under formula I.

The reactions can be performed in solvents or diluents that are inert to the reactants, such as in the case of (a) in benzene, toluene, dioxane, ethyl acetate or chloroform; or in the case of (b) in nitrobenzene, ether, dioxane or tetrahydrofuran. The reaction (b) can be performed also in an excess of hydrofluoric acid as diluent.

Suitable acid-binding agents are, e.g. inorganic bases such as hydroxides and carbonates of alkali metals and alkaline-earth metals, and, in particular, tertiary amines such as triethylamine, dimethylaniline and pyridine bases.

The reactions are performed at a temperature of between −30° and +100° C, preferably between −20° and +10° C, and under normal pressure.

The compounds of formula I are suitable for the control of various pests.

British Pat. No. 1,251,907 describes compounds of the formula

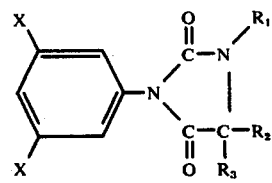

wherein X is a halogen atom; $R_1$ is a hydrogen atom, an alkyl group having 1–5 carbon atoms, or a phenyl group; $R_2$ is a hydrogen atom, an alkyl group having 1–6 carbon atoms which may be substituted with a methylmercapto group, a phenyl group or a benzyl group; and $R_3$ is a hydrogen atom, an alkyl group having 1–6 carbon atoms, or a phenyl group; and their use as microbicides and contains the following passage concerning the relationship between chemical constitution and activity:

"Thus, it has been found surprisingly, that only in cases where halogen atoms have simultaneously been substituted in the 3- and 5-positions of the benzene ring attached to the nitrogen atom of the imide moiety of a 3-phenylimidazolidine-2,4-dione derivative, does the derivative display physiological activities entirely different from those of other homologous compounds; i.e. they have a strong and a wide range of fungicidal activities, and no detrimental action on plants."

It has now surprisingly been found that the compounds of the instant invention though not possessing the allegedly essential 3,5-dichlorophenyl structure nevertheless exhibit excellent microbicidal activity.

The compounds of formula I can therefore be used against both gram-positive and gram-negative bacteria, as well as against ubiquitous fungi, such as Staphylococcus aureus, Escherichia coli, Salmonella sp. and Candida albicans.

The compounds of formula I are effective also against phytopathogenic fungi. These include representatives of the classes Phycomycetes, such as Plasmopara viticola, pythium debaryanum, Ascomycetes such as Venturia inaequalis, Erysiphe graminis, Podosphaera leucotricha; Basidiomycetes such as Rhizoctonia solani, and, in particular, Fungi imperfecti such as Botryis cinerea and Septoria apicola.

The compounds can be employed in vineyards and in the cultivation of fruit and ornamental plants, as well as in crops of useful plants such as cotton, rice, corn and maize, and in other crops.

The compounds have a curative and prophylactic action. The compounds can be used for the protection of seed, or can be applied to parts of the plants themselves, or to the soil.

The agents according to the invention are prepared in a manner known per se by the intimate mixing and/or grinding of active substances of the general formula I with suitable carriers, optionally with the addition of dispersing agents or solvents which are inert to the active substances. The active substances can be obtained and used in the following forms:

solid preparations: dusts, scattering agents, granulates, coated granulates, impregnated granulates and homogeneous granulates;

water-dispersible active-substance concentrates: wettable powders, pastes or emulsions;

liquid preparations: solutions.

Other biocidal active substances or agents can be mixed with described agents according to the invention. For the widening of their sphere of action, the new agents may thus contain, in addition to the stated compounds of the general formula I, for example, insecticides, fungicides, bactericides, fungistatics, bacteriostatics or nematocides. The agents according to the invention can also contain fertilisers, trace elements, etc.. Preparations of the new active substances of the general formula I are described in the following. Parts are expressed as parts by weight.

Dusts

The following substances are used in the preparation of (a) a 5% dust, and (b) a 2% dust:

a. 5 parts of active substance, 95 parts of talcum;

b. 2 parts of active substance, 1 part of highly dispersed silicic acid, 97 parts of talcum.

The active substances are mixed and ground with the carriers.

Granulate

The following substances are used to prepare a 5% granulate:

5: parts of active substance,
0.25: part of epichlorohydrin,
0.25: part of cetyl polyglycol ether,
3.50: parts of polyethylene glycol,
91: parts of kaolin (particle size 0.3 – 0.8 mn).

The active substance is mixed with epichlorohydrin and dissolved with 6 parts of acetone; the polyethylene glycol and cetyl polyglycol ether are then added. The solution thus obtained is sprayed onto kaolin, and the acetone is subsequently evaporated off in vacuo.

Wettable powder

The following constituents are used for the preparation of (a) a 40%, (b) and (c) a 25%, and (d) a 10% wettable powder:

a. 40: parts of active substance,
5: parts of sodium lignin sulphonate,
1: part of sodium dibutyl-naphthalene sulphonate,
54: parts of silicic acid;

b. 25: parts of active substance,
4.5: parts of calcium lignin sulphonate,
1.9: parts of Champagne chalk/hydroxyethyl cellulose mixture (1:1),
1.5: parts of sodium dibutyl naphthalene sulphonate,
19.5: parts of silicic acid,
19.5: parts of Champagne chalk,
28.1: parts of kaolin;

c. 25: parts of active substance,
2.5: parts of isooctylphenoxy-polyoxyethylene-ethanol,
1.7: parts of Champagne chalk/hydroxyethyl cellulose mixture (1:1),
8.3: parts of sodium aluminium silicate,
16.5: parts of kieselguhr,
46: parts of kaolin;

d. 10: parts of active substance,
3: parts of a mixture of the sodium salts of saturated fatty alcohol sulphates,
5: parts of naphthalenesulphonic acid/formaldehyde condensate,
82: parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrate

The following substances are used to prepare a 25% emulsifiable concentrate:

25: parts of active substance,
2.5: parts of epoxidised vegetable oil,
10: parts of an alkylarylsulphonate/fatty alcohol polyglycol ether mixture,
5: parts of dimethylformamide,
57.5: parts of xylene.

It is possible to prepare from these concentrates, by dilution with water, emulsions of any desired concentration.

Dry dressing agent

20: parts of active substance,
1: part of paraffin oil,
79: parts of talcum.

Wet dressing agent

23: parts of active substance,
1.65: parts of alkarylpolyglycol ether (emulsifier),
1.65: parts of $NaHSO_4 \cdot H_2O$, finely ground,
73.7 parts of diethylene glycol monethyl ether acetate.

Furthermore, the active substances of formulae I can be used in the form of solutions, emulsions and suspensions for the preservation of organic materials, such as wood, paper, plastics, coating agents, etc., as well as disinfectants, e.g. in soaps, detergents and rinsing baths.

The antimicrobics mentioned are thus suitable for use as preservatives and disinfectants for commercial products of all kinds, such as glues, binders, coating agents, textile auxiliaries or finishing agents, dyeing and printing pastes and similar preparations based on organic dyestuffs and pigments, also such products containing as additives casein or other organic compounds.

The compounds of the invention can be used as preservatives also in the cellulose and paper industry for, inter alia, the prevention of the known formation of mucilage, caused by microorganisms, in the equipment used for making paper.

The action of the compounds of formula I may be utilised also for imparting to plastics a preserving and disinfecting finish, such as is desired, for instance, for consumer goods of all kinds, such as for foot mats, foot gratings, swimming baths, wall coverings, etc.. By incorporation of the said compounds into the appropriate wax compositions and polishing waxes, there are obtained floor and furniture preserving agents having a disinfecting action.

On account of better solubility in organic solvents, the active substances are also very suitable for application from non-aqueous media. Organic solvents are, for example, trichloroethylene, propylene glycol, methoxyethanol and dimethylformamide, to which can also be added dispersing agents and/or other auxiliaries.

Depending on the purpose of application, the content of active substances of the present invention can be between 0.1 and 50 g, preferably between 1 and 30 g of active substance per litre of treatment liquid.

By combination of the compounds of the invention with interface-active substances, there are obtained detergents and cleansing agents having antibacterial or antimycotic action, such as is desirable in the foodstuff industry, breweries, dairies and slaughterhouses.

The detergents and cleansing agents may be in any desired liquid, pulp-like, solid, flaky or granular form. The compounds of the invention can be incorporated both into anion-active compounds (such as soaps) and into cation-active surfactants or mixtures of various surfactants. The content of active substance in detergents and cleansing agents is in general 0.01 to 5%, in most cases 0.1 to 3%.

For disinfectants and preservatives, the compounds can also be used in combination with known antimicrobial agents.

The following examples further illustrate the invention without limiting its scope. Temperatures are in degrees Centigrade

EXAMPLE 1

Preparation of 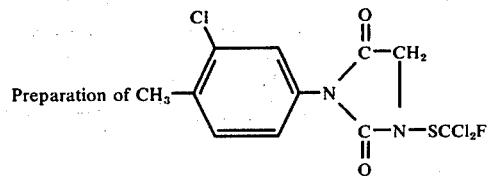

1-(dichlorofluoromethylthio)-3-(3'-chloro-4'-methylphenyl)-imidazolidine-2,4-dione (Compound No. 1).

23.8 g of fluorodichloromethanesulphenyl chloride in 100 ml of acetic acid ethyl ester is added dropwise within 20 minutes at −10° C, with vigorous stirring, to a suspension of 22.5 g of 3-(3'-chloro-4'-methylphenyl)-imidazolidine-2,4-dione in 400 ml of acetic acid ethyl ester, and after one hour there is also added dropwise, at 0° C in the course of 10 minutes, 14.2 g of triethylamine in 100 ml of acetic acid ethyl ester; the cooling bath is subsequently removed and stirring is continued for 3 hours at room temperature. The triethylamine hydrochloride that has precipitated is filtered off and then washed with 100 ml of acetic acid ethyl ester; the solvent is evaporated off in vacuo to obtain, after recrystallisation in methanol, Compound No. 1 which melts at 166° – 167° C.

EXAMPLE 2

Preparation of 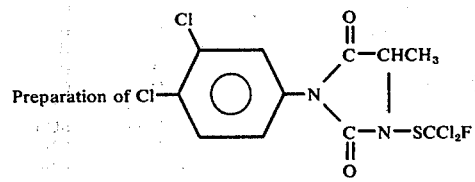

1-(dichlorofluoromethylthio)-3-(3',4'-dichlorophenyl)-5-methylimidazolidine-2,4-dione (Compound 2).

20.4 g of fluorodichloromethanesulphenyl chloride is added dropwise at 0° C, with thorough stirring, to 25.9 g of 3-(3',4'-dichlorophenyl)-5-methyl-imidazolidine-2,4-dione in 500 ml of acetic acid ethyl ester, and after 2 hours an addition is made dropwise, likewise at 0° C. of 12.1 g of triethylamine in 100 ml of acetic acid ethyl ester. After the whole has been stirred for 3 hours at room temperature, the triethylamine hydrochloride is filtered off; the solvent is evaporated off from the filtrate and the residue is recrystallised in methanol. Compound No. 2 melts at 138°– 140° C after recrystallisation.

The following compounds are prepared in an analogous manner.

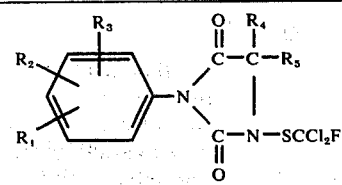

| Comp. No. | $R_1$ | $R_2$ | $R_3$ | $R_4$ | $R_5$ | Physical data |
|---|---|---|---|---|---|---|
| 3 | 3'-Cl | 4'-CF$_3$ | H | H | H | M.P. 163–164° |
| 4 | 4'-NO$_2$ | H | H | H | H | |

-continued

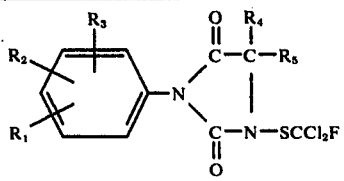

| Comp. No. | R₁ | R₂ | R₃ | R₄ | R₅ | Physical data |
|---|---|---|---|---|---|---|
| 5 | 4'-OCH₃ | H | H | H | H | |
| 6 | 4'-CF₃ | H | H | H | H | M.P. 187–188° |
| 7 | 3'-Cl | 4'-Cl | H | H | H | M.P. 147–149° |
| 8 | 3'-Cl | H | H | H | H | M.P. 117–121° |
| 9 | 2'-Cl | 5'-Cl | H | H | H | M.P. 105–106° |
| 10 | 2'-CF₃ | H | H | H | H | M.P. 81–82° |
| 11 | 3'-CF₃ | H | H | H | H | M.P. 122–123° |
| 12 | 2'-CH₃ | H | H | H | H | M.P. 112–113° |
| 13 | 2'-CH₃ | 4'-Cl | H | H | H | M.P. 128–130° |
| 14 | 2'-NO₂ | 4'-Cl | H | H | H | |
| 15 | 2'-Cl | 4'-C₂H₅O | H | H | H | |
| 16 | 2'-Cl | 4'-Cl | 5'Cl | H | H | |
| 17 | 2'-CH₃ | 4'-Cl | 6'-Cl | H | H | |
| 18 | 2'-CF₃ | 4'-Cl | H | H | H | |
| 19 | 2'-F | H | H | H | H | |
| 20 | 4'-F | H | H | H | H | |
| 21 | 4'-Cl | H | H | H | H | M.P. 190–191° |
| 22 | 4'-I | H | H | H | H | |
| 23 | 3'-Cl | 4'-C₃H₇(i) | H | H | H | |
| 24 | 2'-NO₂ | 4'-NO₂ | H | H | H | |
| 25 | 3'-CH₃ | H | H | H | H | |
| 26 | H | H | H | H | H | |
| 27 | 2'-CH₃ | 4'-CH₃ | 6'-CH₃ | H | H | |
| 28 | 2'-CH₃ | 6'-CH₃ | H | H | H | M.P. 125–127° |
| 29 | 2'-C₂H₅ | 6'-C₂H₅ | H | H | H | |
| 30 | 2'-F | 4'-Cl | 6'-Cl | H | H | |
| 31 | 2'-Cl | 4'-Cl | 6'-NO₂ | H | H | |
| 32 | 3'-CF₃ | 5'-CF₃ | H | H | H | |
| 33 | 2'-OCH₃ | 5'-OCH₃ | H | H | H | |
| 34 | 4'-OC₃H₇(i) | H | H | H | H | |
| 35 | 2'-Br | 4'-CH₃ | H | H | H | oil |
| 36 | 4'-Cl | H | H | CH₃ | H | M.P. 169–171° |
| 37 | 3'-Cl | 4'-Cl | H | CH₃ | CH₃ | M.P. 85–86° |
| 38 | 2'-Cl | 5'-Cl | H | i-C₃H₇ | H | M.P. 96–97° |
| 39 | 3'-Cl | H | H | CH₃ | H | |
| 40 | 4'-Cl | H | H | CH₃ | CH₃ | |
| 41 | 2'-CF₃ | H | H | CH₃ | H | |
| 42 | 3'-CF₃ | 5'-CF₃ | H | C₂H₅ | CH₃ | |
| 43 | 3'-Cl | 4'-Cl | H | i-C₃H₇ | H | M.P. 82–83° |
| 44 | 3'-Cl | 4'-CH₃ | H | CH₃ | H | |
| 45 | 3'-Cl | H | H | CH₃ | CH₃ | |
| 46 | 2'-Cl | 5'-Cl | H | CH₃ | H | |
| 47 | 2'-Cl | 5'-Cl | H | CH₃ | CH₃ | M.P. 119–120° |
| 48 | 3'-CF₃ | 5'-CF₃ | H | CH₃ | H | |
| 49 | 2'-F | H | H | n-C₃H₇ | H | |
| 50 | 2'-CF₃ | H | H | i-C₃H₇ | H | |
| 51 | 3'-Cl | H | H | i-C₃H₇ | H | |
| 52 | 3'-Cl | 4'-CH₃ | H | i-C₃H₇ | H | |
| 53 | 2'-Cl | 4'-Cl | 5'-Cl | CH₃ | CH₃ | |
| 54 | 3'-Cl | 4'-CH₃ | H | CH₃ | CH₃ | |
| 55 | 2'-CH₃ | 6'-CH₃ | H | CH₃ | H | |
| 56 | 2'-CH₃ | 6'-C₂H₅ | H | i-C₃H₇ | H | |
| 57 | 2'-OCH₃ | H | H | CH₃ | CH₃ | |
| 58 | 3'i-C₃H₇ | 4'-Cl | H | CH₃ | H | |
| 59 | 2'-OCH₃ | 3'-Cl | 5'-Cl | H | H | |
| 60 | 2'-OCH₃ | 3'-Cl | 5'-Cl | CH₃ | H | |
| 61 | 2'-OCH₃ | 3'-Cl | 5'-Cl | CH₃ | CH₃ | |
| 62 | 2'-OC₂H₅ | 3'-Cl | 5'-Cl | H | H | |
| 63 | 2'-OC₃H₇(i) | 3'-Cl | 5'-Cl | H | H | |

EXAMPLE 3

Fungicidal action a. Action against Botrytis cinerea on Vicia faba

Vicia plants, about 10 cm in height, were sprayed with a spray emulsion (0.05% active substance) prepared from a wettable powder of the active substance. After 48 hours, the treated plants were infected with a conidiospore suspension of the fungus. An assessment of fungus infestation was made after an incubation of the infected plants during 3 days with 95–100% relative humidity at 21° C.

b. Action against Venturia inaequalis on Malus sylvestris

Apple cuttings having new shoots 10–20 cm in length were sprayed with a spray emulsion (0.05% active substance) prepared from a wettable powder of the active substance. After 24 hours, the treated plants were infected with a conidiospore suspension of the fungus. The plants were then incubated for 5 days with 90–100% relative humidity, and for a further 10 days allowed to stand in a greenhouse at 20°–24° C. An evaluation of scab infestation was made 15 days after the plants had been infected.

c. Action against Plasmopara viticola on Vitis vinifera

Grape-vine cuttings in the 6-8-leaf stage were sprayed with a spray emulsion (0.05% of active substance) prepared from a wettable powder of the active substance. After 24 hours, the treated plants were infected with a sporangium suspension of the fungus. After an incubation time of 6 days at 20° C with 95-100% relative humidity, an assessment was made of fungus infestation.

d. Action against Podosphaera leucotricha on Malus sylvestris

Apple cuttings having new shoots about 15 cm in length were sprayed with a spray emulsion (0.05% of active substance) prepared from a wettable powder of the active substance. After 24 hours, the treated plants were infected with a conidiospore suspension of the fungus, and then stored in a controlled-atmosphere chamber at 20° C with 70% relative humidity. The extent of fungus infestation was assessed 12 days after the plants had been infected.

e. Action against Erysiphe graminis on Herdeum vulgare

Barley plants about 8 cm in height were sprayed with a spray emulion (0.05% o active substance) prepared from a wettable powder of the active substance. After 48 hours, the treated plants were dusted with conidiospores of the fungus. The infected barley plants were stored in a greenhouse at about 22° C. and the fungus infestation was evaluated after 10 days.

f. Action against Septoria apicola on Apium graveolens

Celery plants 10-15 cm in height were sprayed with a spray emulsion (0.05% of active substance) prepared from a wettable powder of the active substance. After 24 hours the treated plants were infected with a conidiospore suspension of the fungus. The plants were subsequently allowed to stand for 5 days in a greenhouse at 20°-24° C. An assessment of fungus infestation was made 15 days after the plants had been infected.

The following compounds exhibited a good action against the fungi listed below (i.e. infestation of plants was less that 20% of that in the case of he untreated but infected control plants):

Botrytis cinerea: Compounds Nos. 1, 2, 3, 6, 7, 8, 9, 12, 13, 21 and 36.
Venturia inaequalis: Compounds Nos. 7,9,11 and 21.
Plasmopara viticola: Compounds Nos. 9 and 13.
Septoria apicola: Compounds Nos. 9, 6 and 8.
Podosphaera leucotricha: Compound No. 10.
Frysiphe graminis: Compound No. 10.

EXAMPLE 4

Action against Pythium debaryanum

An inoculum is prepared from infected oat grains and distilled water, and is then mixed into sterile soil (ca. 120 ml of oat grains / 1 kg of soil). 30 g of soil in each case is placed into a Petri dish. The test substance is suspended in a nutrient solution of malt/peptone/water. This solution is transferred, at a concentration corresponding to 500 ppm (relative to the volume of soil), by pipette to the soil. The samples are then incubated for 7 days at 20° to 24° C.

An evaluation is made on the basis of the occurring fungus growth.

In the case of Pythium debaryanum, no fungus growth occurred with application of Compound No. 28.

Gradient-plate test for determining antimicrobial effectiveness

[Method: W. Szybalski et al., J. Bact. 64, 489 (1952)] 30 $cm^3$ of a liquid agar solution containing 100 ppm of test substance is poured onto a wedge-shaped layer of agar (30 $cm^3$) in a flat 100 × 100 × 15 mm glass vessel. During cooling of the solution, the active substance partially diffuses into the lower agar layer. There is thus obtained a concentration gradient in the direction of the greatest thickness of the lower agar layer. Standardised suspensions of bacteria or fungi are applied, parallel to the concentration gradient, onto the surface of the combined layers of agar. After incubation of the culture for 24 hours at 37° C (bacteria) or 72 hours at 28° C (fungi), a complete prevention of microbial growth was effected in the case of the following organisms by application of the stated compounds at a concentration of 100 ppm or less.

| Organism | Compound Nos. |
| --- | --- |
| Staphylococcus aureus | 2,7,8,9,10,12,28 |
| Streptococcus faecalis | 7,8,9,10,12,28 |
| Bacillus subtilis | 2,7,8,9,10,12,28 |
| Candida albicans | 7,8,9,10,12,28 |
| Trichophyton mentagrophytes | 2,7,8,9,10,12,28 |
| Aspergillus elegans | 2,7,8,9,10,12,28 |
| Erwinia salicis | 8,9,10,12,28 |
| Escherichia coli | 7,8,9,10,12,28 |
| Proteus vulgaris | 8,9,10,12,28 |
| Pseudomonas solanacearum | 8,9,10,12,28 |
| Pseudomonas lachrymans | 9,28 |
| Xanthomonas vesicatoria | 7,8,9,10,12,28 |

I claim:

1. A composition for controlling bacteria and fungi comprising (1) a bactericidally effective amount of a compound of the formula

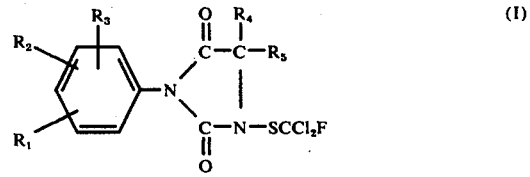

wherein each of $R_1$ and $R_2$ represents hydrogen, halogen, $C_1$-$C_3$ alkyl, nitro, $C_1$-$C_3$ haloalkyl or $C_1$-$C_3$ alkoxy; $R_3$ represents hydrogen, halogen or methyl; and each of $R_4$ and $R_5$ represents hydrogen or $C_1$-$C_3$; and wherein, if one of $R_1$, $R_2$ or $R_3$ is hydrogen, the other two cannot simultaneously be halogen in the metaposition with respect to the amino group; and (2) a carrier.

2. A composition according to claim 1 in which, in the compound, each of $R_1$ and $R_2$ represents hydrogen, chlorine, methyl or trifluoromethyl; $R_3$ represents hydrogen, chlorine or methyl; and $R_4$ and $R_5$ represent hydrogen.

3. A method for combatting bacteria and fungi which comprises applying thereto a bactericidally or fungicidally effective amount of a compound according to claim 1.

4. A method according to claim 3 in which, in the compound, $R_4$ and $R_5$ represent hydrogen.

5. A method according to claim 3 in which, in the compound, each of $R_1$ and $R_2$ represents hydrogen, chlorine, methyl or trifluoromethyl; and $R_3$ represents hydrogen, chlorine or methyl.

6. A method according to claim 5 in which the compound is 1-dichlorofluoromethylthio-3-(3',4'-dichlorophenyl)-5-methylimidazoline-2,4-dione.

7. A method according to claim 5 in which the compound is 1-dichlorofluoromethylthio-3-(4'-chlorophenyl)-5-methylimidazoline-2,4-dione.

8. A method according to claim 4 in which the compound is 1-dichlorofluoromethylthio-3-(2',5'-dichlorophenyl)-imidazoline-2,4-dione.

9. A method according to claim 4 in which the compound is 1-dichlorofluoromethylthio-3-(3'-chlorophenyl)-imidazoline-2,4-dione.

10. A method according to claim 4 in which the compound is 1-dichlorofluoromethylthio-3-(3',4'-dichlorophenyl)-imidazoline-2,4-dione.

11. A method according to claim 4 in which the compound is 1-dichlorofluoromethylthio-3-(2',6'-dimethylphenyl)-imidazoline-2,4-dione.

* * * * *